US008278318B2

(12) United States Patent
Yao et al.

(10) Patent No.: US 8,278,318 B2
(45) Date of Patent: Oct. 2, 2012

(54) SPIROCYCLES AS INHIBITORS OF 11-BETA HYDROXYL STEROID DEHYDROGENASE TYPE 1

(75) Inventors: Wenqing Yao, Kennett Square, PA (US); Jincong Zhuo, Boothwyn, PA (US); Colin Zhang, Ambler, PA (US)

(73) Assignee: Incyte Corporation, Wilmington, DE (US)

( * ) Notice: Subject to any disclaimer, the term of this patent is extended or adjusted under 35 U.S.C. 154(b) by 936 days.

(21) Appl. No.: 12/143,427

(22) Filed: Jun. 20, 2008

(65) Prior Publication Data

US 2008/0318991 A1 Dec. 25, 2008

Related U.S. Application Data

(60) Provisional application No. 60/945,487, filed on Jun. 21, 2007.

(51) Int. Cl.
*A61K 31/438* (2006.01)
*C07D 401/10* (2006.01)
*C07D 401/04* (2006.01)

(52) U.S. Cl. .......................................... 514/278; 546/17
(58) Field of Classification Search .................. 546/18, 546/17; 514/278
See application file for complete search history.

(56) References Cited

U.S. PATENT DOCUMENTS

| | | | |
|---|---|---|---|
| 4,439,606 A | 3/1984 | Du et al. | |
| 5,442,064 A | 8/1995 | Pieper et al. | |
| 5,614,534 A | 3/1997 | Binet et al. | |
| 5,633,247 A | 5/1997 | Baldwin et al. | |
| 5,668,138 A | 9/1997 | Baziard-Mouysset et al. | |
| 5,852,029 A | 12/1998 | Fisher et al. | |
| 5,981,754 A | 11/1999 | Badone et al. | |
| 6,547,958 B1 | 4/2003 | Elomari et al. | |
| 2003/0229119 A1 | 12/2003 | Kym et al. | |
| 2004/0097511 A1 | 5/2004 | Habashita et al. | |
| 2005/0020645 A1 | 1/2005 | Ohta et al. | |
| 2005/0080078 A1 | 4/2005 | Aquila et al. | |
| 2005/0282858 A1 | 12/2005 | Yao et al. | |
| 2005/0288308 A1 | 12/2005 | Amrien et al. | |
| 2005/0288317 A1 | 12/2005 | Yao et al. | |
| 2005/0288329 A1 | 12/2005 | Yao et al. | |
| 2005/0288338 A1 | 12/2005 | Yao et al. | |
| 2006/0004049 A1 | 1/2006 | Yao et al. | |
| 2006/0009471 A1 | 1/2006 | Yao et al. | |
| 2006/0009491 A1 | 1/2006 | Yao et al. | |
| 2006/0019977 A1 | 1/2006 | Habashita et al. | |
| 2006/0106045 A1 | 5/2006 | Hughes et al. | |
| 2006/0116382 A1 | 6/2006 | Yao et al. | |
| 2006/0122197 A1 | 6/2006 | Yao et al. | |
| 2006/0122210 A1 | 6/2006 | Yao et al. | |
| 2006/0149070 A1 | 7/2006 | Rohde et al. | |
| 2006/0199816 A1 | 9/2006 | Gillespie et al. | |
| 2007/0066584 A1 | 3/2007 | Yao et al. | |
| 2007/0129345 A1 | 6/2007 | Zhuo et al. | |
| 2007/0179142 A1 | 8/2007 | Yao et al. | |
| 2007/0197506 A1 | 8/2007 | Yao et al. | |
| 2007/0197530 A1 | 8/2007 | Li et al. | |
| 2007/0208001 A1 | 9/2007 | Zhuo et al. | |
| 2007/0213311 A1 | 9/2007 | Li et al. | |
| 2007/0270424 A1 | 11/2007 | Li et al. | |
| 2007/0293529 A1 | 12/2007 | Li et al. | |

FOREIGN PATENT DOCUMENTS

| | | |
|---|---|---|
| EP | 0743312 | 11/1996 |
| EP | 1683797 | 7/2006 |
| RU | 2110518 C1 | 5/2008 |
| RU | 2375351 C2 | 8/2008 |
| RU | 2008116844 A | 11/2009 |
| RU | 2008125068 A | 12/2009 |
| RU | 2009118488 A | 12/2009 |
| RU | 2392272 C2 | 6/2010 |
| RU | 2417989 C2 | 5/2011 |
| WO | WO92/06975 A1 | 4/1992 |
| WO | WO 97/11940 | 4/1997 |
| WO | WO0130780 A2 | 5/2001 |
| WO | WO0200196 A2 | 1/2002 |
| WO | WO 03/037847 | 5/2003 |
| WO | WO 03/057698 | 7/2003 |
| WO | WO03010138 A3 | 12/2003 |
| WO | WO 2004056745 | 7/2004 |
| WO | WO2004058727 A1 | 7/2004 |
| WO | WO 2004065351 | 8/2004 |
| WO | WO 2004082687 | 9/2004 |
| WO | WO 2004089470 | 10/2004 |
| WO | WO 2004089896 | 10/2004 |
| WO | WO 2005047286 | 5/2005 |
| WO | WO 2005063745 | 7/2005 |
| WO | WO2005084667 A1 | 9/2005 |
| WO | WO2006/000371 A2 | 1/2006 |
| WO | WO 2006012226 | 2/2006 |
| WO | WO 2006020598 | 2/2006 |
| WO | WO2006/034804 A1 | 4/2006 |
| WO | WO 2006047196 | 5/2006 |
| WO | WO 2006053024 | 5/2006 |
| WO | WO2007/041052 A2 | 4/2007 |

(Continued)

OTHER PUBLICATIONS

International Preliminary Report on Patentability dated Dec. 22, 2009 for International Application No. PCT/US2008/067637 (7 pgs.).
Alberts et al. Endocrinology (2003) 144: 4755-4762.
Albiston et al. (1994) Mol. Cell. Endocrin. 105: R11-R17.
Barf et al. (2002) J. Med. Chem. 45: 3813-3815.
Bellows et al. (1998) Bone 23: 119-125.
Bhargava et al., (2001), Endo 142: 1587-1594.
Billaudel and Sutter (1979) Horm. Metab. Res. 11: 555-560.
Blum, et al., (2003) Prog. Nucl. Acid Res. Mol. Biol. 75:173-216.
Bujalska et al. (1997) Lancet 349: 1210-1213.
Canalis (1996) J. Clin. Endocrinol. Metab. 81: 3441-3447.

(Continued)

*Primary Examiner* — Rita Desai
(74) *Attorney, Agent, or Firm* — Fish & Richardson P.C.

(57) ABSTRACT

The present invention relates to certain spirocyclic compounds that are inhibitors of 11-β hydroxyl steroid dehydrogenase type 1 (11βHSD1), compositions containing the same, and methods of using the same for the treatment of diabetes, obesity and other diseases.

6 Claims, No Drawings

FOREIGN PATENT DOCUMENTS

| WO | WO2007/061978 A1 | 5/2007 |
| WO | WO 2007067504 | 6/2007 |
| WO | WO2008/003611 A1 | 1/2008 |
| WO | WO2008/046758 A2 | 4/2008 |

OTHER PUBLICATIONS

Conn, (1955), J. Lab. Clin. Med. 45: 6-17.
Cooper et al. (2000) Bone 27: 375-381.
Davani et al. (2000) J. Biol. Chem. 275: 34841-34844.
Database CAPLUS on STN (Columbus, OH, USA) No. 126:317635, "Alpha-amino acids derived from ornithine as building blocks for peptide synthesis" abstract, Gescrinier et al. j. Pep. Res. 49(2):183-189 (1997).
Database CAPLUS on STN (Columbus, OH, USA) No. 143:78479, "Preparation of amino acid derivatives as novel M3 muscarinic acetylcholine receptor antagonists" abstract, Busch et al. (2005), see RN 902149-23-9 and 854750-92-8.
Edwards et al. (1988) Lancet 2: 986-989.
Engeli, et al., (2004) Obes. Res. 12: 9-17.
Funder et al. (1988), Science 242: 583-585.
Greene, et al., Protective Groups in Organic Synthesis, 2d. Ed., Wiley & Sons, 1991*.
Gu et al., "Discovery of 4-heteroarylbicyclo[2.2.2]octyltriazoles as potent and selective inhibitors of 11β-HSD1: Novel therapeutic agents for the treatment of metabolic syndrome," *Bioorg. Med. Chem. Lett.*, 15:5266-5269 (2005).
Jausons-Loffreda et al. J. Biolumin and Chemilumin, 9:217-221 (1994).
Journal of Pharmaceutical Science, 66, 2 (1977).
Kotelevstev et al. (1997) Proc. Natl. Acad. Sci. 94: 14924-14929.
Kurukulasuriya , et al., (2003) Curr. Med. Chem. 10: 123-53.
Li, Y. et al. Syntheses and SAR of piperidin-3-yl ureas as potent and selective 11β-HSD-1 inhibitors, MEDI 54 Abstract of Presentation at the 233$^{rd}$ ACS National Meeting, Chicago, IL, Mar. 25-29, 2007.
Li, Y. et al Syntheses and SAR of Piperidin-3-yl Ureas as Potent and Selective 11β-HSD-1 inhibitors, Presentation at the 233$^{rd}$ ACS National Meeting, Chicago, IL, Mar. 25-29, 2007.
Lindsay et al. (2003) J. Clin. Endocrinol. Metab. 88: 2738-2744.
Livingstone et al. (2000) Endocrinology 131: 560-563.
Low et al. (1994) J. Mol. Endocrin. 13: 167-174.
Lupien et al. (1998) Nat. Neurosci. 1: 69-73.
Masuzaki et al. (2001) Science 294: 2166-2170.
Masuzaki et al. (2003) J. Clinical Invest. 112: 83-90.
Masuzaki, et al., (2003) Curr. Drug Targets Immune Endocr. Metabol. Disord. 3: 255-62.
Matsuzawa et al. (1999) Ann. N.Y. Acad. Sci. 892: 146-154.
McEwen and Sapolsky (1995) Curr. Opin. Neurobiol. 5: 205-216.
Miller and Chrousos (2001) Endocrinology and Metabolism, eds. Felig and Frohman (McGraw-Hill, New York), 4th Ed.: 387-524.
Morton et al. (2001) J. Biol. Chem. 276: 41293-41300.
Morton et al. (2004) Diabetes 53: 931-938.
Ogawa et al. (1992) J. Clin. Invest. 90: 497-504.
Pitt et al., New England J. Med. (1999), 341: 709-719.
Pitt et al., New England J. Med. (2003), 348: 1309-1321.
Rajan et al. (1996) J. Neurosci. 16: 65-70.
Rask et al. (2001) J. Clin. Endocrinol. Metab. 86: 1418-1421.
Rauz et al. (2001) Invest. Ophthalmol. Vis. Sci. 42: 2037-2042.
Reaven (1993) Ann. Rev. Med. 44: 121-131.
Remington's Pharmaceutical Sciences, 17th ed., Mack Publishing Company, Easton, Pa., 1985, p. 1418.
Stokes et al. (2000) Invest. Ophthalmol. Vis. Sci. 41: 1629-1683.
T. Higuchi and V. Stella, "Pro-drugs as Novel Delivery Systems," vol. 14 of the A.C.S. Symposium Series, and in Bioreversible Carriers in Drug Design, ed. Edward B. Roche, American Pharmaceutical Association and Pergamon Press, 1987*.
Wajchenberg (2000) Endocr. Rev. 21: 697-738.
Wake et al. (2003) J. Clin. Endocrinol. Metab. 88: 3983-3988.
Walker et al. (1979) Hypertension 1: 287-291.
Wilson et al. (1998) Proc. Natl. Acad. Sci. 95: 10200-10205.
Yau et al. (2001) Proc. Natl. Acad. Sci. 98: 4716-4721.
Yao, W. et al. Discovery of potent and selective 11β-HSD-1 Inhibitors, MEDI 228 Abstract of Presentation at the 233$^{rd}$ ACS National Meeting, Chicago, IL, Mar. 25-29, 2007.
Yao, W. Discovery of Potent and Orally Active Inhibitors of 11β-Hydroxysteroid Dehydrogenase I, presentation at the 233$^{rd}$ ACS National Meeting, Chicago, IL, Mar. 27, 2007.
Yeh et al., "Discovery of orally active butyrolactam 11β-HSD1 inhibitors," *Bioorg. Med. Chem. Lett.*, 16:5555-5560 (2006).
Yeh et al., "Synthesis and biological evaluation of heterocycle containing adamantine 11β-HSD1 inhibitors," *Bioorg. Med. Chem. Lett.*, 16:5414-5419 (2006).
Zhuo, J. et al. Discovery and synthesis of nipecotic amide as novel, potent and selective 11β-HSD-1- inhibitors MEDI 48 Abstract, 233$^{rd}$ ACS National Meeting, Chicago, IL, Mar. 25-29, 2007.
Zhuo, J. et al. Discovery of Nipecotic Amides as Novel, Potent and Selective 11βHSD1 Inhibitors, poster at the 233$^{rd}$ ACS National Meeting, Chicago, IL, Mar. 25-29, 2007.
International Search Report for PCT/US05/28201.
Eurasian Patent Search Report for related application No. 200701036.
International Search Report for PCT/US2008/067637 dated Sep. 17, 2008.
International Search Report and Written Opinion for PCT/US05/40550, dated Mar. 26, 2007.
Georgia Patent Office, Search Report for Georgian Patent Application AP200811654, Jun. 17, 2011 (6 pages).
Blom et al, 'Preparative LC-MS Purification: Improved Compound Specific Method Optimization,' J. Combi. Chem., 6, 874-883, (2004).
Lineth Magaly Fallas CORDERO, Opposition filed on behalf of Asociacion de la Industria Farmaceutica Nactional—ASIFAN dated May 18, 2010 for Costa Rican Patent Appln. No. 11183 (with English translation) (11 pgs.).
Sandeep et al., '11B-Hydroxysteroid dehydrogenase inhibition improves cognitive function in healthy elderly men and type 2 diabetics,' Proc. Natl. Acad. Sci., Early Edition: 1-6, (2004).
Lemke et al; Foye's Principles of Medicinal Chemistry, 6th Edition, Wolters Kluwer, USA, 2008, p. 50.
Office Action; Colombian Patent Office, Colombian Application No. 09-149.800, Aug. 16, 2012, 8 pgs.

SPIROCYCLES AS INHIBITORS OF 11-BETA HYDROXYL STEROID DEHYDROGENASE TYPE 1

CROSS-REFERENCE TO RELATED APPLICATIONS

This application claims the benefit of U.S. Ser. No. 60/945,487, filed Jun. 21, 2007, the disclosure of which is incorporated herein by reference in its entirety.

FIELD OF THE INVENTION

The present invention relates to certain spirocyclic compounds that are inhibitors of 11-β hydroxyl steroid dehydrogenase type 1 (11βHSD1), compositions containing the same, and methods of using the same for the treatment of diabetes, obesity and other diseases.

BACKGROUND OF THE INVENTION

The importance of the hypothalamic-pituitary-adrenal (HPA) axis in controlling glucocorticoid excursions is evident from the fact that disruption of homeostasis in the HPA axis by either excess or deficient secretion or action results in Cushing's syndrome or Addison's disease, respectively (Miller and Chrousos (2001) Endocrinology and Metabolism, eds. Felig and Frohman (McGraw-Hill, New York), 4$^{th}$ Ed.: 387-524). Patients with Cushing's syndrome (a rare disease characterized by systemic glucocorticoid excess originating from the adrenal or pituitary tumors) or receiving glucocorticoid therapy develop reversible visceral fat obesity. Interestingly, the phenotype of Cushing's syndrome patients closely resembles that of Reaven's metabolic syndrome (also known as Syndrome X or insulin resistance syndrome) the symptoms of which include visceral obesity, glucose intolerance, insulin resistance, hypertension, type 2 diabetes and hyperlipidemia (Reaven (1993) Ann. Rev. Med. 44: 121-131). However, the role of glucocorticoids in prevalent forms of human obesity has remained obscure because circulating glucocorticoid concentrations are not elevated in the majority of metabolic syndrome patients. In fact, glucocorticoid action on target tissue depends not only on circulating levels but also on intracellular concentration, locally enhanced action of glucocorticoids in adipose tissue and skeletal muscle has been demonstrated in metabolic syndrome. Evidence has accumulated that enzyme activity of 11βHSD1, which regenerates active glucocorticoids from inactive forms and plays a central role in regulating intracellular glucocorticoid concentration, is commonly elevated in fat depots from obese individuals. This suggests a role for local glucocorticoid reactivation in obesity and metabolic syndrome.

Given the ability of 11βHSD1 to regenerate cortisol from inert circulating cortisone, considerable attention has been given to its role in the amplification of glucocorticoid function. 11βHSD1 is expressed in many key GR-rich tissues, including tissues of considerable metabolic importance such as liver, adipose, and skeletal muscle, and, as such, has been postulated to aid in the tissue-specific potentiation of glucocorticoid-mediated antagonism of insulin function. Considering a) the phenotypic similarity between glucocorticoid excess (Cushing's syndrome) and the metabolic syndrome with normal circulating glucocorticoids in the latter, as well as b) the ability of 11βHSD1 to generate active cortisol from inactive cortisone in a tissue-specific manner, it has been suggested that central obesity and the associated metabolic complications in syndrome X result from increased activity of 11βHSD1 within adipose tissue, resulting in 'Cushing's disease of the omentum' (Bujalska et al. (1997) Lancet 349: 1210-1213). Indeed, 11βHSD1 has been shown to be upregulated in adipose tissue of obese rodents and humans (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Additional support for this notion has come from studies in mouse transgenic models. Adipose-specific overexpression of 11βHSD1 under the control of the aP2 promoter in mouse produces a phenotype remarkably reminiscent of human metabolic syndrome (Masuzaki et al. (2001) Science 294: 2166-2170; Masuzaki et al. (2003) J. Clinical Invest. 112: 83-90). Importantly, this phenotype occurs without an increase in total circulating corticosterone, but rather is driven by a local production of corticosterone within the adipose depots. The increased activity of 11βHSD1 in these mice (2-3 fold) is very similar to that observed in human obesity (Rask et al. (2001) J. Clin. Endocrinol. Metab. 86: 1418-1421). This suggests that local 11βHSD1-mediated conversion of inert glucocorticoid to active glucocorticoid can have profound influences whole body insulin sensitivity.

Based on this data, it would be predicted that the loss of 11βHSD1 would lead to an increase in insulin sensitivity and glucose tolerance due to a tissue-specific deficiency in active glucocorticoid levels. This is, in fact, the case as shown in studies with 11βHSD1-deficient mice produced by homologous recombination (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). These mice are completely devoid of 11-keto reductase activity, confirming that 11βHSD1 encodes the only activity capable of generating active corticosterone from inert 11-dehydrocorticosterone. 11βHSD1-deficient mice are resistant to diet- and stress-induced hyperglycemia, exhibit attenuated induction of hepatic gluconeogenic enzymes (PEPCK, G6P), show increased insulin sensitivity within adipose, and have an improved lipid profile (decreased triglycerides and increased cardio-protective HDL). Additionally, these animals show resistance to high fat diet-induced obesity. Taken together, these transgenic mouse studies confirm a role for local reactivation of glucocorticoids in controlling hepatic and peripheral insulin sensitivity, and suggest that inhibition of 11βHSD1 activity may prove beneficial in treating a number of glucocorticoid-related disorders, including obesity, insulin resistance, hyperglycemia, and hyperlipidemia.

Data in support of this hypothesis has been published. Recently, it was reported that 11βHSD1 plays a role in the pathogenesis of central obesity and the appearance of the metabolic syndrome in humans. Increased expression of the 11βHSD1 gene is associated with metabolic abnormalities in obese women and that increased expression of this gene is suspected to contribute to the increased local conversion of cortisone to cortisol in adipose tissue of obese individuals (Engeli, et al., (2004) Obes. Res. 12: 9-17).

A new class of 11βHSD1 inhibitors, the arylsulfonamidothiazoles, was shown to improve hepatic insulin sensitivity and reduce blood glucose levels in hyperglycemic strains of mice (Barf et al. (2002) J. Med. Chem. 45: 3813-3815; Alberts et al. Endocrinology (2003) 144: 4755-4762). Furthermore, it was recently reported that selective inhibitors of 11βHSD1 can ameliorate severe hyperglycemia in genetically diabetic obese mice. Thus, 11βHSD1 is a promising pharmaceutical target for the treatment of the Metabolic Syndrome (Masuzaki, et al., (2003) Curr. Drug Targets Immune Endocr. Metabol. Disord. 3: 255-62).

A. Obesity and Metabolic Syndrome

As described above, multiple lines of evidence suggest that inhibition of 11βHSD1 activity can be effective in combating obesity and/or aspects of the metabolic syndrome cluster, including glucose intolerance, insulin resistance, hyperglycemia, hypertension, and/or hyperlipidemia. Glucocorticoids are known antagonists of insulin action, and reductions in local glucocorticoid levels by inhibition of intracellular cortisone to cortisol conversion should increase hepatic and/or peripheral insulin sensitivity and potentially reduce visceral adiposity. As described above, 11βHSD1 knockout mice are resistant to hyperglycemia, exhibit attenuated induction of key hepatic gluconeogenic enzymes, show markedly increased insulin sensitivity within adipose, and have an improved lipid profile. Additionally, these animals show resistance to high fat diet-induced obesity (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). Thus, inhibition of 11βHSD1 is predicted to have multiple beneficial effects in the liver, adipose, and/or skeletal muscle, particularly related to alleviation of component(s) of the metabolic syndrome and/or obesity.

B. Pancreatic Function

Glucocorticoids are known to inhibit the glucose-stimulated secretion of insulin from pancreatic beta-cells (Billaudel and Sutter (1979) Horm. Metab. Res. 11: 555-560). In both Cushing's syndrome and diabetic Zucker fa/fa rats, glucose-stimulated insulin secretion is markedly reduced (Ogawa et al. (1992) J. Clin. Invest. 90: 497-504). 11βHSD1 mRNA and activity has been reported in the pancreatic islet cells of ob/ob mice and inhibition of this activity with carbenoxolone, an 11βHSD1 inhibitor, improves glucose-stimulated insulin release (Davani et al. (2000) J. Biol. Chem. 275: 34841-34844). Thus, inhibition of 11βHSD1 is predicted to have beneficial effects on the pancreas, including the enhancement of glucose-stimulated insulin release.

C. Cognition and Dementia

Mild cognitive impairment is a common feature of aging that may be ultimately related to the progression of dementia. In both aged animals and humans, inter-individual differences in general cognitive function have been linked to variability in the long-term exposure to glucocorticoids (Lupien et al. (1998) Nat. Neurosci. 1: 69-73). Further, dysregulation of the HPA axis resulting in chronic exposure to glucocorticoid excess in certain brain subregions has been proposed to contribute to the decline of cognitive function (McEwen and Sapolsky (1995) Curr. Opin. Neurobiol. 5: 205-216). 11βHSD1 is abundant in the brain, and is expressed in multiple subregions including the hippocampus, frontal cortex, and cerebellum (Sandeep et al. (2004) Proc. Natl. Acad. Sci. Early Edition: 1-6). Treatment of primary hippocampal cells with the 11βHSD1 inhibitor carbenoxolone protects the cells from glucocorticoid-mediated exacerbation of excitatory amino acid neurotoxicity (Rajan et al. (1996) J. Neurosci. 16: 65-70). Additionally, 11βHSD1-deficient mice are protected from glucocorticoid-associated hippocampal dysfunction that is associated with aging (Yau et al. (2001) Proc. Natl. Acad. Sci. 98: 4716-4721). In two randomized, double-blind, placebo-controlled crossover studies, administration of carbenoxolone improved verbal fluency and verbal memory (Sandeep et al. (2004) Proc. Natl. Acad. Sci. Early Edition: 1-6). Thus, inhibition of 11βHSD1 is predicted to reduce exposure to glucocorticoids in the brain and protect against deleterious glucocorticoid effects on neuronal function, including cognitive impairment, dementia, and/or depression.

D. Intra-Ocular Pressure

Glucocorticoids can be used topically and systemically for a wide range of conditions in clinical ophthalmology. One particular complication with these treatment regimens is corticosteroid-induced glaucoma. This pathology is characterized by a significant increase in intra-ocular pressure (IOP). In its most advanced and untreated form, IOP can lead to partial visual field loss and eventually blindness. IOP is produced by the relationship between aqueous humour production and drainage. Aqueous humour production occurs in the non-pigmented epithelial cells (NPE) and its drainage is through the cells of the trabecular meshwork. 11βHSD1 has been localized to NPE cells (Stokes et al. (2000) Invest. Ophthalmol. Vis. Sci. 41: 1629-1683; Rauz et al. (2001) Invest. Ophthalmol. Vis. Sci. 42: 2037-2042) and its function is likely relevant to the amplification of glucocorticoid activity within these cells. This notion has been confirmed by the observation that free cortisol concentration greatly exceeds that of cortisone in the aqueous humour (14:1 ratio). The functional significance of 11βHSD1 in the eye has been evaluated using the inhibitor carbenoxolone in healthy volunteers (Rauz et al. (2001) Invest. Ophthalmol. Vis. Sci. 42: 2037-2042). After seven days of carbenoxolone treatment, IOP was reduced by 18%. Thus, inhibition of 11βHSD1 in the eye is predicted to reduce local glucocorticoid concentrations and IOP, producing beneficial effects in the management of glaucoma and other visual disorders.

E. Hypertension

Adipocyte-derived hypertensive substances such as leptin and angiotensinogen have been proposed to be involved in the pathogenesis of obesity-related hypertension (Matsuzawa et al. (1999) Ann. N.Y. Acad. Sci. 892: 146-154; Wajchenberg (2000) Endocr. Rev. 21: 697-738). Leptin, which is secreted in excess in aP2-11βHSD1 transgenic mice (Masuzaki et al. (2003) J. Clinical Invest. 112: 83-90), can activate various sympathetic nervous system pathways, including those that regulate blood pressure (Matsuzawa et al. (1999) Ann. N.Y. Acad. Sci. 892: 146-154). Additionally, the renin-angiotensin system (RAS) has been shown to be a major determinant of blood pressure (Walker et al. (1979) Hypertension 1: 287-291). Angiotensinogen, which is produced in liver and adipose tissue, is the key substrate for renin and drives RAS activation. Plasma angiotensinogen levels are markedly elevated in aP2-11βHSD1 transgenic mice, as are angiotensin II and aldosterone (Masuzaki et al. (2003) J. Clinical Invest. 112: 83-90). These forces likely drive the elevated blood pressure observed in aP2-11βHSD1 transgenic mice. Treatment of these mice with low doses of an angiotensin II receptor antagonist abolishes this hypertension (Masuzaki et al. (2003) J. Clinical Invest. 112: 83-90). This data illustrates the importance of local glucocorticoid reactivation in adipose tissue and liver, and suggests that hypertension may be caused or exacerbated by 11βHSD1 activity. Thus, inhibition of 11βHSD1 and reduction in adipose and/or hepatic glucocorticoid levels is predicted to have beneficial effects on hypertension and hypertension-related cardiovascular disorders.

F. Bone Disease

Glucocorticoids can have adverse effects on skeletal tissues. Continued exposure to even moderate glucocorticoid doses can result in osteoporosis (Cannalis (1996) J. Clin. Endocrinol. Metab. 81: 3441-3447) and increased risk for fractures. Experiments in vitro confirm the deleterious effects of glucocorticoids on both bone-resorbing cells (also known as osteoclasts) and bone forming cells (osteoblasts).

11βHSD1 has been shown to be present in cultures of human primary osteoblasts as well as cells from adult bone, likely a mixture of osteoclasts and osteoblasts (Cooper et al. (2000) Bone 27: 375-381), and the 11βHSD1 inhibitor carbenoxolone has been shown to attenuate the negative effects of glucocorticoids on bone nodule formation (Bellows et al. (1998) Bone 23: 119-125). Thus, inhibition of 11βHSD1 is predicted to decrease the local glucocorticoid concentration within osteoblasts and osteoclasts, producing beneficial effects in various forms of bone disease, including osteoporosis.

Small molecule inhibitors of 11βHSD1 are currently being developed to treat or prevent 11βHSD1-related diseases such as those described above. For example, certain amide-based inhibitors are reported in WO 2004/089470, WO 2004/089896, WO 2004/056745, and WO 2004/065351. Additional small molecule inhibitors of 11βHSD1 are reported in US 2005/0282858, US 2006/0009471, US 2005/0288338, US 2006/0009491, US 2006/0004049, US 2005/0288317, US 2005/0288329, US 2006/0122197, US 2006/0116382, and US 2006/0122210. 11) INCY0035 (US 2007/0066584)

Antagonists of 11βHSD1 have been evaluated in human clinical trials (Kurukulasuriya, et al., (2003) Curr. Med. Chem. 10: 123-53).

In light of the experimental data indicating a role for 11βHSD1 in glucocorticoid-related disorders, metabolic syndrome, hypertension, obesity, insulin resistance, hyperglycemia, hyperlipidemia, type 2 diabetes, androgen excess (hirsutism, menstrual irregularity, hyperandrogenism) and polycystic ovary syndrome (PCOS), therapeutic agents aimed at augmentation or suppression of these metabolic pathways, by modulating glucocorticoid signal transduction at the level of 11βHSD1 are desirable.

As evidenced herein, there is a continuing need for new and improved drugs that target 11βHSD1. The compounds, compositions and methods described herein help meet this and other needs.

SUMMARY OF THE INVENTION

The present invention provides, inter alia, inhibitors of 11βHSD1 having Formula I:

I or pharmaceutically acceptable salts thereof, wherein the variables are defined below.

The present invention further provides compositions comprising a compound of Formula I, or a pharmaceutically acceptable salt thereof, and at least one pharmaceutically acceptable carrier.

The present invention further provides methods of inhibiting 11βHSD1 by contacting the 11βHSD1 with a compound of Formula I, or a pharmaceutically acceptable salt thereof.

The present invention further provides methods of inhibiting activity of 11βHSD1 comprising contacting the 11βHSD1 with a compound of Formula I, or a pharmaceutically acceptable salt thereof.

The present invention further provides methods of inhibiting the conversion of cortisone to cortisol in a cell comprising contacting the cell with a compound of Formula I, or a pharmaceutically acceptable salt thereof.

The present invention further provides methods of inhibiting the production of cortisol in a cell comprising contacting the cell with a compound of Formula I, or a pharmaceutically acceptable salt thereof.

The present invention further provides methods of treating various diseases including any one of the following disorders, or any combination of two or more of the following disorders: obesity; diabetes; glucose intolerance; insulin resistance; hyperglycemia; hypertension; hyperlipidemia; cognitive impairment; depression; dementia; glaucoma; cardiovascular disorders; osteoporosis; inflammation; metabolic syndrome; androgen excess; or polycystic ovary syndrome (PCOS) in a patient comprising administering to the patient a therapeutically effective amount of a compound of Formula I, or a pharmaceutically acceptable salt thereof.

DETAILED DESCRIPTION

The present invention provides, inter alia, inhibitors of 11βHSD1 having Formula I:

I or pharmaceutically acceptable salts thereof, wherein:
$R^1$ is F, Cl, Br, or I; and
$R^2$ and $R^3$ are independently selected from H, $C_{1-6}$ alkyl, and $C_{3-6}$ cycloalkyl.

In some embodiments:
$R^1$ is F and Cl; and
$R^2$ and $R^3$ are independently selected from H and $C_{1-4}$ alkyl.

In some embodiments, $R^1$ is F or Cl.
In some embodiments, $R^1$ is F.
In some embodiments, $R^1$ is Cl.
In some embodiments, $R^2$ and $R^3$ are independently selected from H, methyl, and ethyl.
In some embodiments, at least one of $R^2$ and $R^3$ is other than H.
In some embodiments, the compounds of the invention have Formula II:

II

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

As used herein, "cycloalkyl" refers to non-aromatic 3-7 membered carbocycles including, for example, cyclopropyl, cyclobutyl, cyclopentyl, and cyclohexyl.

The compounds described herein are asymmetric (e.g., having one or more stereocenters). All stereoisomers, such as enantiomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Cis and trans isomers of the compounds of the present invention are described and may be isolated as a mixture of isomers or as separated isomeric forms.

Compounds of the invention can also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, amide—imidic acid pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

All compounds, and pharmaceutically acceptable salts thereof, may be obtained in various solid forms, including solvated or hydrated forms. In some embodiments, the solid form is a crystalline form. Methods for preparing and discovering different solid forms are routine in the art and include, for example, X-ray powder diffraction, differential scanning calorimetry, thermogravimetric analysis, dynamic vapor sorption, FT-IR, Raman scattering methods, solid state NMR, Karl-Fischer titration, etc.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Compounds of the invention can modulate activity of 11βHSD1. The term "modulate" is meant to refer to an ability to increase or decrease activity of an enzyme or receptor. Accordingly, compounds of the invention can be used in methods of modulating 11βHSD1 by contacting the enzyme or receptor with any one or more of the compounds or compositions described herein. In some embodiments, compounds of the present invention can act as inhibitors of 11βHSD1. In further embodiments, the compounds of the invention can be used to modulate activity of 11βHSD1 in an individual in need of modulation of the enzyme or receptor by administering a modulating amount of a compound of the invention.

The present invention further provides methods of inhibiting the conversion of cortisone to cortisol in a cell, or inhibiting the production of cortisol in a cell, where conversion to or production of cortisol is mediated, at least in part, by 11βHSD1 activity. Methods of measuring conversion rates of cortisone to cortisol and vice versa, as well as methods for measuring levels of cortisone and cortisol in cells, are routine in the art.

The present invention further provides methods of increasing insulin sensitivity of a cell by contacting the cell with a compound of the invention. Methods of measuring insulin sensitivity are routine in the art.

The present invention further provides methods of treating disease associated with activity or expression, including abnormal activity and overexpression, of 11βHSD1 in an individual (e.g., patient) by administering to the individual in need of such treatment a therapeutically effective amount or dose of a compound of the present invention, or pharmaceutically acceptable salt thereof, or a pharmaceutical composition thereof Example diseases can include any disease, disorder or condition that is directly or indirectly linked to expression or activity of the enzyme. An 11βHSD1-associated disease can also include any disease, disorder or condition that can be prevented, ameliorated, or cured by modulating enzyme activity.

Examples of 11βHSD1-associated diseases include obesity, diabetes, glucose intolerance, insulin resistance, hyperglycemia, hypertension, hyperlipidemia, cognitive impairment, dementia, depression (e.g., psychotic depression), glaucoma, cardiovascular disorders, osteoporosis, and inflammation. Further examples of 11βHSD1-associated diseases include metabolic syndrome, type 2 diabetes, androgen excess (hirsutism, menstrual irregularity, hyperandrogenism) and polycystic ovary syndrome (PCOS).

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal. In some embodiments, the cell is an adipocyte, a pancreatic cell, a hepatocyte, neuron, or cell comprising the eye (ocular cell).

As used herein, the term "contacting" refers to the bringing together of indicated moieties in an in vitro system or an in vivo system. For example, "contacting" the 11βHSD1 enzyme with a compound of the invention includes the administration of a compound of the present invention to an individual or patient, such as a human, having 11βHSD1, as well as, for example, introducing a compound of the invention into a sample containing a cellular or purified preparation containing the 11βHSD1 enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

When employed as pharmaceuticals, the compounds of the invention can be administered in the form of pharmaceutical compositions which is a combination of a compound of the invention and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, for example see International Patent Application No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, vaccines, antibodies, immune enhancers, immune suppressants, anti-inflammatory agents, analgesics, and drugs for the treatment of diabetes or obesity, hyperglycemia, hypertension, hyperlipidemia, and the like. Agents for treatment of metabolic disorders with which a compound of the invention could be combined include, but are not limited to, amylin analogues, incretin mimetics, inhibitors of the incretin-degrading enzyme dipeptidyl peptidase-IV, agonists of peroxisome proliferator-activated receptor (PPAR)-a and PPAR-g, and CB1 cannabinoid receptor inhibitors.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

All compounds were purified by either flash column chromatography or reversed-phase liquid chromatography using a Waters FractionLynx LC-MS system with mass directed fractionation. Column: Waters XBridge $C_{18}$ 5 µm, 19×100 mm; mobile phase A: 0.15% $NH_4OH$ in water and mobile phase B: 0.15% $NH_4OH$ in acetonitrile; the flow rate was 30 ml/m, the separating gradient was optimized for each compound using the Compound Specific Method Optimization protocol as described in literature ["Preparative LC-MS Purification:

Improved Compound Specific Method Optimization", K. Blom, B. Glass, R. Sparks, A. Combs, J. Combi. Chem., 2004, 6, 874-883].

The separated product was then typically subjected to analytical LC/MS for purity check under the following conditions: Instrument; Agilent 1100 series, LC/MSD, Column: Waters Sunfire™ $C_{18}$ 5 μm, 2.1×5.0 mm, Buffers: mobile phase A: 0.025% TFA in water and mobile phase B: 0.025% TFA in acetonitrile; gradient 2% to 80% of buffer B in 3 min with flow rate 1.5 mL/min.

Example 1

5-{3-Fluoro-4-[(5S)-2-(cis-4-hydroxycyclohexyl)-1-oxo-2,7-diazaspiro[4.5]dec-7-yl]phenyl}-N-methylpyridine-2-carboxamide

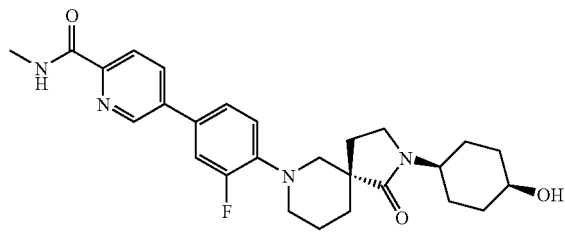

Step 1: 1-benzyl 3-ethylpiperidine-1,3-dicarboxylate

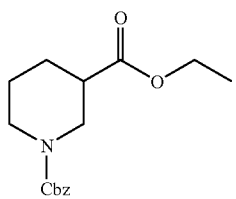

Benzyl chloroformate (Aldrich, cat #:119938) (191 mL, 1.34 mol) was slowly added to a cooled (at 0° C.) mixture of ethyl piperidine-3-carboxylate (Aldrich, cat #:194360) (200 g, 1.27 mol) and triethylamine (266 mL, 1.91 mol) in methylene chloride (1000 mL). The reaction mixture was allowed to gradually warm to ambient temperature and stirred for 3 h. The reaction was quenched by the addition of 1N HCl aq. solution and the product was extracted several times with methylene chloride. The combined extracts were washed with water, saturated aq. NaHCO$_3$, water, brine, dried over MgSO$_4$, filtered and concentrated under reduced pressure to afford the desired product as oil (359.8 g, 97%). LC/MS 292.2 (M+H)$^+$.

Step 2: 1-benzyl 3-ethyl 3-(3-methylbut-2-en-1-yl)piperidine-1,3-dicarboxylate

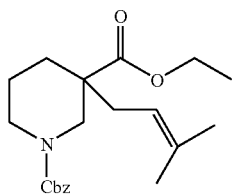

To a solution of 1-benzyl 3-ethyl piperidine-1,3-dicarboxylate (120.0 g, 0.412 mol) in THF (400 ml) cooled at −78° C. was added dropwise 270 mL of sodium bis(trimethylsilyl)amide solution (1M solution in THF from Aldrich, cat #:245585) over 2 h. The mixture was stirred at −78° C. for additional 1 h. Then 1-bromo-3-methylbut-2-ene (Aldrich cat #: 249904) (71 mL, 0.62 mol) was added slowly over 1 h. The mixture was stirred at −78° C. for 30 min, and allowed to warm to r.t. and stirred for an additional 3 h. The reaction mixture was quenched with 1N HCl aq. solution. Most of THF was removed under reduced pressure. The residue was extracted with ethyl acetate. The combined extracts were washed with sat. aq. NaHCO$_3$ and brine, then dried over MgSO$_4$, filtered and concentrated under reduced pressure. The crude residue was purified by flash column chromatography on a silica gel column with 10~20% ethyl acetate in hexane to yield the desired product (140 g, 94%). LC/MS: m/e=332.2 (M+H)$^+$.

Step 3: 1-benzyl 3-ethyl 3-(2-oxoethyl)piperidine-1,3-dicarboxylate

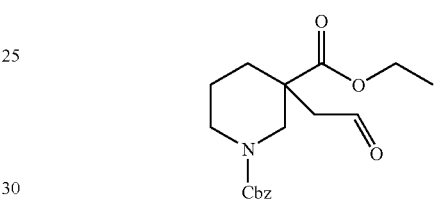

Ozone was passed through a solution of 1-benzyl 3-ethyl 3-(3-methylbut-2-en-1-yl)piperidine-1,3-dicarboxylate (35.2 g, 0.0979 mol) in methylene chloride (800 mL) at −78° C. until the color of the solution turned blue. The reaction mixture was then flushed with nitrogen until the blue color dissipated. Dimethylsulfide (Aldrich, cat #: 274380) (14 mL, 0.19 mol) and triethylamine (26.5 mL, 0.19 mol) were added and the mixture was stirred at ambient temperature overnight. The volatile solvent were removed under reduced pressure and purified directly by flash chromatography on a silica gel column with 20% ethyl acetate in hexanes to afford the desired product in quantitative yield. LC/MS 334.2 (M+H)$^+$.

Step 4: Benzyl 2-(cis-4-hydroxycyclohexyl)-1-oxo-2,7-diazaspiro[4.5]decane-7-carboxylate

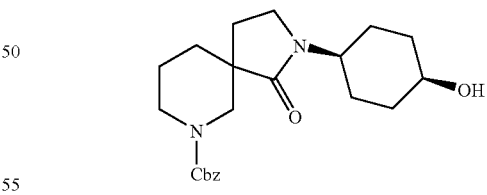

To a suspension of cis-4-aminocyclohexanol hydrochloride (Available from Sijia Medchem Lab, China) (13.8 g, 0.0910 mol) and 1-benzyl 3-ethyl 3-(2-oxoethyl)piperidine-1,3-dicarboxylate (31.0 g, 0.0930 mol) in 1,2-dichloroethane (250 mL) was added triethylamine (23.3 mL, 0.167 mol) at room temperature. The mixture was stirred at 40° C. overnight. Sodium triacetoxyborohydride (Aldrich, cat #: 316393) (49.3 g, 0.232 mol) was added to the above mixture and stirred at r.t. for 1 h. LC/MS data indicated that the starting material was consumed, and an intermediate product with m/e: 433.2 (M+H)$^+$ was observed.

The mixture was then heated at 80° C. for 4 h or until LC/MS showed the intermediate amine (m/e: 433.2) was consumed. The reaction mixture was quenched with aq. NaHCO$_3$. The organic layer was washed with brine, dried over MgSO$_4$, filtered and concentrated under reduced pressure. The crude material was dried under reduced pressure overnight to give colorless viscous oil (26.9 g, 66.8%). LC/MS m/e 387.2 (M+H)$^+$.

Step 5: Benzyl (5S)-2-(cis-4-hydroxycyclohexyl)-1-oxo-2,7-diazaspiro[4.5]decane-7-carboxylate

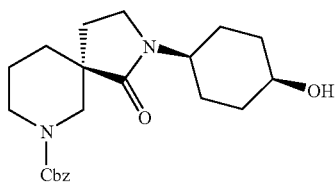

The racemic mixture obtained from above step (26.9 g) was purified on an Agilent 1100 series preparatory system using a Chiralcel OD-H column (3.0×25 cm, 5 micron particle size, Chiral Technologies) eluting with 30% ethanol/hexanes (isocratic, 22 mL/min.). The column loading was approximately 150 mg/injection and peak collection was triggered by UV absorbance at 220 nM. Peak 1 eluted at approximately at 8.5 min. and Peak 2 eluted at approximately 9.8 min. The fractions of Peak 2 were combined and concentrated to provide the desired product (11.9 g) as a white foamy solid. The optical purity of the pooled material from peak 2 was determined by using an Agilent 1100 series analytical system equipped with a Chiralcel OD-H column (4.6×250 mm, 5 micron particle size, Chiral Technologies) and eluting with 30% ethanol/hexanes (isocratic, 0.8 mL/min.). LC/MS m/e 387.2 (M+H)$^+$. The absolute stereochemistry of the peak 2 was established based on X-ray single crystal structure determination of close analogs: Benzyl (5S)-2-(trans-4-hydroxycyclohexyl)-1-oxo-2,7-diazaspiro[4.5]decane-7-carboxylate and (5S)-2-(cis-4-{[tert-butyl(dimethyl)silyl]oxy}cyclohexyl)-2,7-diazaspiro[4.5]decan-1-one prepared as described in Steps 5a-c.

Step 5a: Benzyl 2-(cis-4-{[tert-butyl(dimethyl)silyl]oxy}cyclohexyl)-1-oxo-2,7-diazaspiro[4.5]decane-7-carboxylate

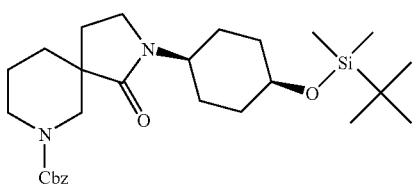

To a stirred solution of benzyl 2-(cis-4-hydroxycyclohexyl)-1-oxo-2,7-diazaspiro[4.5]decane-7-carboxylate (60.00 g, 155.2 mmol) in anhydrous N,N-dimethylformamide (160 mL) at r.t. was added 1H-imidazole (32.0 g, 466 mmol) and tert-butyldimethylsilyl chloride (36.2 g, 233 mmol). The reaction mixture was stirred at r.t. for 4 h, quenched with water (150 mL), and extracted with EtOAc (3×150 mL). The combined organic layers were washed with brine, dried over sodium sulfate, filtered and concentrated under reduced pressure to afford the crude product (84 g). The pure product (55.4 g) was obtained by re-crystallization of the crude product from heptane. The mother liquor was concentrated and subjected to purification by flash chromatography on a silical gel column eluting with AcOEt/Haxane to give additional 14.4 g of the product with a total 89.7% yield.

Step 5b: 2-(cis-4-{[tert-butyl(dimethyl)silyl]oxy}cyclohexyl)-2,7-diazaspiro[4.5]decan-1-one

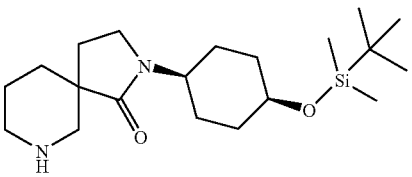

To a solution of benzyl 2-(cis-4-{[tert-butyl(dimethyl)silyl]oxy}cyclohexyl)-1-oxo-2,7-diazaspiro[4.5]decane-7-carboxylate (18.0 g, 35.9 mmol) in methanol (150 mL) was added 10% palladium on carbon (Aldrich, cat #: 520888) (1.8 g, 1.5 mmol) under the atmosphere of nitrogen. The reaction mixture was hydrogenated and shaken at 50 psi for 20 h. The reaction mixture was filtered through a pad of Celite and then washed with methanol (300 mL). The filtrate was concentrated under reduced pressure to give the desired product as a white solid in quantitative yield.

Step 5c: (5S)-2-(cis-4-{[tert-butyl(dimethyl)silyl]oxy}cyclohexyl)-2,7-diazaspiro[4.5]decan-1-one

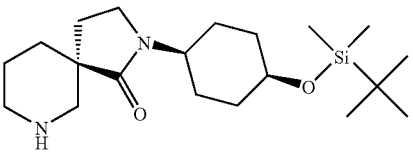

2-(cis-4-{[tert-Butyl(dimethyl)silyl]oxy}cyclohexyl)-2,7-diazaspiro[4.5]decan-1-one (7.00 g, 19.1 mmol) was dissolved in acetonitrile (50 mL) and methanol (7 mL) at r.t. After the starting material was completely dissolved, the solution was heated up to 70° C. To the above solution was slowly added a solution of (2R)-hydroxy(phenyl)acetic acid (1.45 g, 9.55 mmol) in acetonitrile (20 mL) at 65-70° C. After addition, the solution was heated at 74° C. for 10 min, and allowed to cool slowly to room temperature overnight. The crystalline formed was collected by filtration to afford 3.38 g of the desired product as (2R)-hydroxy(phenyl)acetic acid salt. The resulting salt (3.38 g) was dissolved in water (50 mL), and adjusted to pH~12 with 40 mL aq K$_2$CO$_3$ solution (2.0 M). The mixture was extracted with dichloromethane (3 times). The combined organic layers were dried with magnesium sulfate, filtered, and concentrated under reduced pressure to afford the desired product as a free base (colorless crystalline solid) (2.37 g). The absolute stereochemistry of this compound was established by X-ray single crystal structure determination of (2R)-hydroxy(phenyl)acetic acid salt of (5S)-2-(cis-4-{[tert-butyl(dimethyl)silyl]oxy}cyclohexyl)-2,7-diazaspiro[4.5]decan-1-one.

Step 6: (5S)-2-(cis-4-hydroxycyclohexyl)-2,7-diazaspiro[4.5]decan-1-one

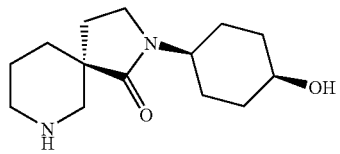

Benzyl (5S)-2-(cis-4-hydroxycyclohexyl)-1-oxo-2,7-diazaspiro[4.5]decane-7-carboxylate prepared in Step 5 (0.266 g, 0.000688 mol) was dissolved in methanol (5.0 mL) and stirred under an atmosphere of hydrogen in the presence of 10% palladium on carbon (Aldrich, cat #: 520888) (20.0 mg) at r.t. for 2 h. The reaction mixture was filtered and the volatile solvents were removed under reduced pressure to afford the desired product in quantitative yield. LC/MS m/e 253.2 (M+H)$^+$.

Step 7: (5S)-7-(4-bromo-2-fluorophenyl)-2-(cis-4-hydroxycyclohexyl)-2,7-diazaspiro[4.5]decan-1-one

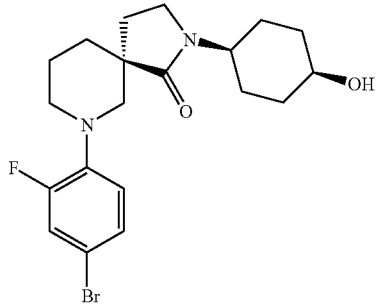

A mixture of (5S)-2-(cis-4-hydroxycyclohexyl)-2,7-diazaspiro[4.5]decan-1-one (1.04 g, 0.00412 mol), 4-bromo-2-fluoro-1-iodobenzene (Aldrich, cat #: 283304) (1.85 g, 0.00615 mol), copper(I) iodide (Aldrich, cat #: 215554) (0.122 g, 0.000640 mol), potassium phosphate (2.63 g, 0.0124 mol) and 1,2-ethanediol (0.48 mL, 0.0086 mol) in 1-butanol (3.90 mL) was heated at 100° C. under nitrogen for 2 d. The reaction was quenched with water, and extracted with ether. The organic layers were combined, washed with water, brine, dried over Na$_2$SO$_4$, and filtered. The filtrate was evaporated under reduced pressure. The residue was purified by flash column chromatography on a silica gel column eluting with 0 to 5% methanol in DCM to yield the desired product (950 mg, 54.2%). LC/MS m/e 425.1/427.0 (M+H)$^+$.

Step 8: 5-3-fluoro-4-[(5S)-2-(cis-4-hydroxycyclohexyl)-1-oxo-2,7-diazaspiro[4.5]dec-7-yl]phenyl-N-methylpyridine-2-carboxamide Potassium phosphate (637 mg, 0.00300 mol) in water (3.00 mL) was added to a mixture of (5S)-7-(4-bromo-2-fluorophenyl)-2-(cis-4-hydroxycyclohexyl)-2,7-diazaspiro[4.5]decan-1-one (425 mg, 0.00100 mol), N-methyl-5-(4,4,5,5-tetramethyl-1,3,2-dioxaborolan-2-yl)pyridine-2-carboxamide (Frontier Inc., cat #: M10074) (393 mg, 0.00150 mol) and tetrakis(triphenylphosphine)palladium (Aldrich, cat #: 216666) (35 mg, 0.000030 mol) in 1,4-dioxane (3.00 mL). The resulting mixture was heated at 120° C. for 24 h. The mixture was diluted with ethyl acetate and washed with water and brine. The organic layer was dried over Na$_2$SO$_4$, filtered, concentrated under reduced pressure. The residue was purified by flash column chromatography on a silica gel column eluting with 5% methanol in DCM to yield the desired product (285 mg, 59.3%). LC/MS m/e 481.2 (M+H)$^+$. $^1$H-NMR (400 MHz, DMSO-d$_6$): 8.89 (1H, dd, J=2.5, 0.6 Hz), 8.76 (1H, q, J=4.7 Hz), 8.22 (1H, dd, J=8.4, 2.5 Hz), 8.03 (1H, dd, J=8.4, 0.6 Hz), 7.65 (1H, dd, J=14.2, 2.1 Hz), 7.56 (1H, dd, J=8.5, 2.1 Hz), 7.13 (1H, t, J=8.5 Hz), 4.37 (1 H, d, J=3.1 Hz), 3.78 (1H, m), 3.71 (1H, m), 3.21-3.38 (3H, m), 3.07 (1H, d, J=11.4 Hz), 2.81 (3H, d, J=4.7 Hz), 2.64-2.74 (2H, m), 2.18-2.26 (1H, m), 1.60-1.91 (8H, m), 1.39-1.51 (3H, m), 1.21-1.30 (2H, m).

Example 2

5-{3-Fluoro-4-[(5S)-2-(cis-4-hydroxycyclohexyl)-1-oxo-2,7-diazaspiro[4.5]dec-7-yl]phenyl}-N,N-dimethylpyridine-2-carboxamide

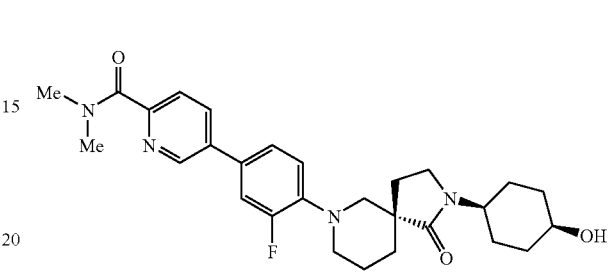

Step 1: 5-bromo-N,N-dimethylpyridine-2-carboxamide

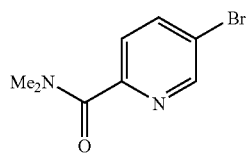

Oxalyl chloride (20.0 mL, 0.236 mol) was added to a solution of 5-bromopyridine-2-carboxylic acid (Alfa Aesar, cat #: B25675) (10.1 g, 0.0500 mol) in methylene chloride (60 mL) at r.t. followed by 5 drops of DMF. The mixture was stirred at r.t. for 2 h. The volatiles were evaporated under reduced pressure. The residue was azotropically evaporated with toluene twice. The residue was then dissolved in DCM (30 mL) followed by the addition of 30 mL of dimethylamine in THF solution (2.0 M) (Aldrich, cat #: 391956) and Hunig's base (20.0 mL) (Aldrich, cat #: 496219). The mixture was stirred at r.t. for 3 h. The reaction mixture was diluted with DCM (100 mL) and washed with water, 1N HCl and brine. The organic phase was dried over Na$_2$SO$_4$, filtered and concentrated to give the desired product (10.5 g, 91.7%).

Step 2: N,N-dimethyl-5-(4,4,5,5-tetramethyl-1,3,2-dioxaborolan-2-yl)pyridine-2-carboxamide

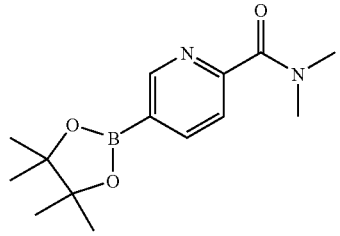

A mixture of 5-bromo-N,N-dimethylpyridine-2-carboxamide (5.73 g, 0.0250 mol), 4,4,5,5,4',4',5',5'-octamethyl-[2,2']bi[[1,3,2]dioxaborolanyl] (6.98 g, 0.0275 mol) (Aldrich, cat #: 473294), [1,1'-bis(diphenylphosphino)ferrocene]dichloropalladium(II) complexed with dichloromethane (1:1) (0.6 g, 0.0007 mol) (Aldrich, cat #: 379670), 1,1'-bis (diphenylphosphino)ferrocene (0.4 g, 0.8 mmol) (Aldrich, cat #: 177261), and potassium acetate (7.36 g, 0.0750 mol) in 1,4-dioxane (100 mL) was heated at 120° C. for 20 h. After cooling, the mixture was concentrated, diluted with ethyl acetate and washed with sat'd NH$_4$Cl solution, water, brine; dried over Na$_2$SO$_4$. After filtration, the filtrate was concentrated and the crude material was further purified on a silica gel column eluting with ethyl acetate/hexane to give the desired product (4.7 g, 68%).

Step 3: 5-{3-Fluoro-4-[(5S)-2-(cis-4-hydroxycyclohexyl)-1-oxo-2,7-diazaspiro[4.5]dec-7-yl]phenyl}-N,N-dimethylpyridine-2-carboxamide This compound was prepared by using procedures that were analogous to those described for the synthesis of Example 1, Step 8 starting from N,N-dimethyl-5-(4,4,5,5-tetramethyl-1,3,2-dioxaborolan-2-yl)pyridine-2-carboxamide and (5S)-7-(4-bromo-2-fluorophenyl)-2-(cis-4-hydroxycyclohexyl)-2,7-diazaspiro[4.5]decan-1-one. LC/MS m/e 495.3 (M+H)$^+$. $^1$H-NMR (400 MHz, DMSO-d$_6$): 8.86 (1H, d, J=1.7 Hz), 8.15 (1H, dd, J=8.1, 2.3 Hz), 7.51-7.65 (3H, m), 7.12 (1H, t, J=8.9 Hz), 4.37 (1 H, d, J=3.1 Hz), 3.78 (1H, m), 3.71 (1H, m), 3.22-3.38 (3H, m), 3.06 (1H, d, J=11.7 Hz), 3.00 (3H, s), 2.97 (3H, s), 2.64-2.74 (2H, m), 2.18-2.27 (1H, m), 1.60-1.91 (8H, m), 1.39-1.51 (3H, m), 1.22-1.30 (2H, m).

Example 3

N-Ethyl-5-{3-fluoro-4-[(5S)-2-(cis-4-hydroxycyclohexyl)-1-oxo-2,7-diazaspiro[4.5]dec-7-yl]phenyl}pyridine-2-carboxamide

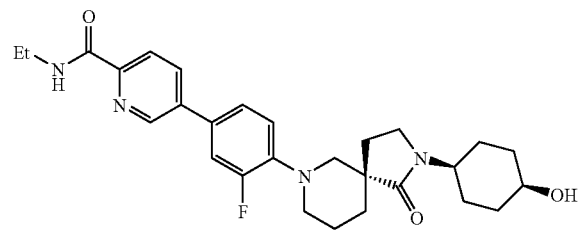

Step 1: N-ethyl-5-(4,4,5,5-tetramethyl-1,3,2-dioxaborolan-2-yl)pyridine-2-carboxamide

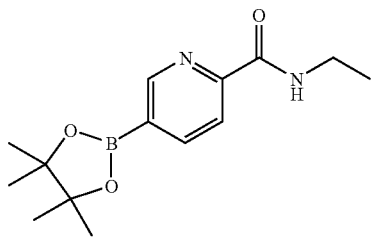

This compound was prepared by using procedures that were analogous to those described for the synthesis of Example 2, Steps 1 & 2 starting from 5-bromopyridine-2-carboxylic acid.

Step 2: N-Ethyl-5-{3-fluoro-4-[(5S)-2-(cis-4-hydroxycyclohexyl)-1-oxo-2,7-diazaspiro[4.5]dec-7-yl]phenyl}pyridine-2-carboxamide This compound was prepared by using procedures that were analogous to those described for the synthesis of Example 1, Step 8 starting from N-ethyl-5-(4,4,5,5-tetramethyl-1,3,2-dioxaborolan-2-yl)pyridine-2-carboxamide and (5S)-7-(4-bromo-2-fluorophenyl)-2-(cis-4-hydroxycyclohexyl)-2,7-diazaspiro[4.5]decan-1-on. LC/MS m/e 495.3 (M+H)$^+$.

Example 4

5-{3-Chloro-4-[(5S)-2-(cis-4-hydroxycyclohexyl)-1-oxo-2,7-diazaspiro[4.5]dec-7-yl]phenyl}-N-ethylpyridine-2-carboxamide

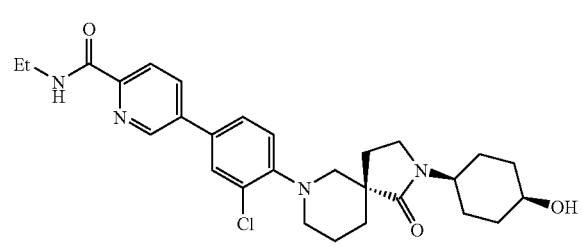

Step 1: (5S)-7-(4-bromo-2-chlorophenyl)-2-(cis-4-{[tert-butyl(dimethyl)silyl]oxy}cyclohexyl)-2,7-diazaspiro[4.5]decan-1-one

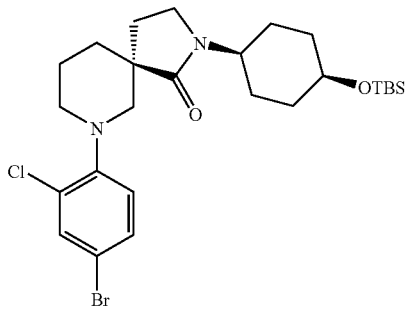

A mixture of (5S)-2-(cis-4-{[tert-butyl(dimethyl)silyl]oxy}cyclohexyl)-2,7-diazaspiro[4.5]decan-1-one (0.282 g, 0.000769 mol), 4-bromo-2-chloro-1-iodobenzene (0.293 g, 0.000922 mol) (Lancaster, cat #: 19245), copper(I) iodide (0.015 g, 0.000077 mol), potassium phosphate (0.490 g, 0.00231 mol) and 1,2-ethanediol (0.0857 mL, 0.00154 mol) in 1-butanol (0.75 mL) was heated at 100° C. under nitrogen for 2 d. The reaction mixture was filtered, concentrated under reduced pressure, and the residue was purified by flash chromatography on a silica gel column (eluting with 0 to 50% ethyl acetate in hexanes) to afford the desired product.

Step 2: 5-{3-chloro-4-[(5S)-2-(cis-4-hydroxycyclohexyl)-1-oxo-2,7-diazaspiro[4.5]dec-7-yl]phenyl}-N-ethylpyridine-2-carboxamide To a stirred mixture of (5S)-7-(4-bromo-2-chlorophenyl)-2-(cis-4-{[tert-butyl(dimethyl)silyl]oxy}cyclohexyl)-2,7-diazaspiro[4.5]decan-1-one (20 mg, 0.00004 mol), [1,1'-bis(diphenylphosphino)ferrocene]dichloropalladium(II) complex with dichloromethane (1:1) (2.0 mg), tetrakis(triphenylphosphine)palladium (1.0 mg) and potassium carbonate (14.9 mg, 0.000108 mol) in anhydrous N,N-dimethylformamide (1 mL) was added N-ethyl-5-(4,4,5,5-tetramethyl-1,3,2-dioxaborolan-2-yl)pyridine-2-carboxamide (14.5 mg, 0.054 mmol). The resulting reaction mixture was heated at 150° C. and stirred overnight, followed by the removal of TBS protecting group by the addition of 1.7 M of fluorosilicic acid in water (0.10 mL) and the mixture was stirred at r.t. overnight. The reaction mixture was then directly purified by RP-HPLC to afford the desired product. LC/MS m/e 511.2 (M+H)$^+$. $^1$H-NMR (400 MHz, DMSO-d$_6$): 8.92 (1H, d, J=2.3 Hz), 8.84 (1H, t, J=5.9 Hz), 8.26 (1H, dd, J=8.2, 2.3 Hz), 8.06 (1H, d, J=8.2 Hz), 7.89 (1H, d, J=2.2 Hz), 7.74 (1H, dd, J=8.5, 2.2 Hz), 7.30 (1H, t, J=8.5 Hz), 4.39 (1 H, d, J=3.1 Hz), 3.80 (1H, m), 3.72 (1H, m), 3.24-3.44 (5H, m), 3.01 (1H, d, J=11.4 Hz), 2.63-2.74 (2H, m), 2.40-2.53 (1H, m), 1.64-1.91 (8H, m), 1.41-1.53 (3H, m), 1.20-1.32 (2H, m), 1.13 (3H, t, J=7.2 Hz).

Example 5

Enzymatic Assay of 11βHSD1

All in vitro assays were performed with clarified lysates as the source of 11βHSD1 activity. HEK-293 transient transfectants expressing an epitope-tagged version of full-length human 11βHSD1 were harvested by centrifugation. Roughly 2×10$^7$ cells were resuspended in 40 mL of lysis buffer (25 mM Tris-HCl, pH 7.5, 0.1 M NaCl, 1 mM MgCl$_2$ and 250 mM sucrose) and lysed in a microfluidizer. Lysates were clarified by centrifugation and the supernatants were aliquoted and frozen.

Inhibition of 11βHSD1 by test compounds was assessed in vitro by a Scintillation Proximity Assay (SPA). Dry test compounds were dissolved at 5 mM in DMSO. These were diluted in DMSO to suitable concentrations for the SPA assay. 0.8 µL of 2-fold serial dilutions of compounds were dotted on 384 well plates in DMSO such that 3 logs of compound concentration were covered. 20 µL of clarified lysate was added to each well. Reactions were initiated by addition of 20 µL of substrate-cofactor mix in assay buffer (25 mM Tris-HCl, pH 7.5, 0.1 M NaCl, 1 mM MgCl$_2$) to final concentrations of 400 µM NADPH, 25 nM $^3$H-cortisone and 0.007% Triton X-100. Plates were incubated at 37° C. for one hour. Reactions were quenched by addition of 40 µL of anti-mouse coated SPA beads that had been pre-incubated with 10 µM carbenoxolone and a cortisol-specific monoclonal antibody. Quenched plates were incubated for a minimum of 30 minutes at RT prior to reading on a Topcount scintillation counter. Controls with no lysate, inhibited lysate, and with no mAb were run routinely. Roughly 30% of input cortisone is reduced by 11βHSD1 in the uninhibited reaction under these conditions.

Example 6

Cell-Based Assay for 11βHSD1 Activity

Peripheral blood mononuclear cells (PBMCS) were isolated from normal human volunteers by Ficoll density centrifugation. Cells were plated at 4×10$^5$ cells/well in 200 µL of AIM V (Gibco-BRL) media in 96 well plates. The cells were stimulated overnight with 50 ng/ml recombinant human IL-4 (R&D Systems). The following morning, 200 nM cortisone (Sigma) was added in the presence or absence of various concentrations of compound. The cells were incubated for 48 hours and then supernatants were harvested. Conversion of cortisone to cortisol was determined by a commercially available ELISA (Assay Design).

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound which is:
   5-{3-Fluoro-4-[(5S)-2-(cis-4-hydroxycyclohexyl)-1-oxo-2,7-diazaspiro[4.5]dec-7-yl]phenyl}-N,N-dimethylpyridine-2-carboxamide;
   or a pharmaceutically acceptable salt thereof.

2. A compound which is:
   5-{3-Fluoro-4-[(5S)-2-(cis-4-hydroxycyclohexyl)-1-oxo-2,7-diazaspiro[4.5]dec-7-yl]phenyl}-N-methylpyridine-2-carboxamide;
   or a pharmaceutically acceptable salt thereof.

3. A composition comprising a compound of claim 1 or claim 2, or a pharmaceutically acceptable salt thereof, and at least one pharmaceutically acceptable carrier.

4. A method of inhibiting activity of 11βHSD1 comprising contacting said 11βHSD1 with a compound of claim 1 or claim 2, or a pharmaceutically acceptable salt thereof.

5. A method of inhibiting the conversion of cortisone to cortisol in a cell comprising contacting the cell with a compound of claim 1 or claim 2, or a pharmaceutically acceptable salt thereof.

6. A method of inhibiting the production of cortisol in a cell comprising contacting the cell with a compound of claim 1 or claim 2, or a pharmaceutically acceptable salt thereof.

* * * * *

UNITED STATES PATENT AND TRADEMARK OFFICE
CERTIFICATE OF CORRECTION

PATENT NO. : 8,278,318 B2  
APPLICATION NO. : 12/143427  
DATED : October 2, 2012  
INVENTOR(S) : Wenqing Yao et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1062 days.

Signed and Sealed this
Fourteenth Day of October, 2014

Michelle K. Lee
*Deputy Director of the United States Patent and Trademark Office*